US010570136B2

(12) United States Patent
De Greef et al.

(10) Patent No.: US 10,570,136 B2
(45) Date of Patent: Feb. 25, 2020

(54) PROCESS FOR THE PREPARATION OF BENZIMIDAZO[1,2-A] BENZIMIDAZOLES

(71) Applicant: UDC IRELAND LIMITED, Dublin (IE)

(72) Inventors: Michiel De Greef, Dublin (IE); Bernd Peter, Dublin (IE); Ruediger Stumpf, Dublin (IE)

(73) Assignee: UDC IRELAND LIMITED, Dublin (IE)

( * ) Notice: Subject to any disclaimer, the term of this patent is extended or adjusted under 35 U.S.C. 154(b) by 0 days.

(21) Appl. No.: 15/739,232

(22) PCT Filed: Jul. 26, 2016

(86) PCT No.: PCT/EP2016/067789
§ 371 (c)(1),
(2) Date: Dec. 22, 2017

(87) PCT Pub. No.: WO2017/017096
PCT Pub. Date: Feb. 2, 2017

(65) Prior Publication Data
US 2018/0170936 A1 Jun. 21, 2018

(30) Foreign Application Priority Data
Jul. 28, 2015 (EP) .................................... 15178573

(51) Int. Cl.
*C07D 487/04* (2006.01)

(52) U.S. Cl.
CPC .................................. *C07D 487/04* (2013.01)

(58) Field of Classification Search
None
See application file for complete search history.

(56) References Cited

FOREIGN PATENT DOCUMENTS

| | | |
|---|---|---|
| WO | 2011160757 A1 | 12/2011 |
| WO | 2012130709 A1 | 10/2012 |
| WO | 2013068376 A1 | 5/2013 |
| WO | 2014009317 A1 | 1/2014 |
| WO | 2014044722 | 3/2014 |
| WO | 2015014791 | 2/2015 |

OTHER PUBLICATIONS

Ku et al. "PLED devices containing triphenylamine-derived polyurethanes as hole-transporting layers exhibit high current efficiencies" J. Mater. Chem. 18 (2008) 1296-1301.

Ponce et al. "Synthesis and Electronic Spectroscopy of Bromocarbazoles. Direct Bromination of N- and C-Substituted Carbazoles by N-Bromosuccinimide or a N-Bromosuccinimide/Silica Gel System" Helvetica Chimica Acta 89 (2006) 1123.

Feng et al. "Synthesis and Optical Properties of Starburst Carbazoles Based on 9-Phenylcarbazole Core" SYNLETT 17 (2006) 2841-2845.

I.V. Kolesnikova et al: "Reactions of N-polyfluorophenylcarbonimidoyl dichlorides with primary and secondary amines. Kinetics and mechanism. Synthesis of polyfluorinated carbodiimides, chloroformamidines, guamidines and benzimidazoles.", Journal of Fluorine Chemistry, vol. 40, No. 2-3, Aug. 1, 1988 (Aug. 1, 1998), pp. 217-246, XP055213650, ISSN: 0022-1139, DOI: 10.1016/S0022-1139(00)83067-5.

Reddouane Achour et al: "Syntheses des Benzimidazolo (1,2-a) Benzimidazoles A Partir des Benzodiazepine-1, 5Ones-2", Bulletin Des Sociétés Chimiques Belges : Vlaamse Chemische Vereniging, Centerick, BE, vol. 96, No. 10, Jan. 1, 1987 (Jan. 1, 1987), pp. 787-792, XP009123274, ISSN: 0037-9646 ; DOI: https://doi.org/10.1002/bscb.19870961010.

Khan, Misbahul Ain; Ribeiro, Vera Lucia Teixeira, "Tetracyclic Heteroaromatic Systems. Part-II. Benzimidazo [1, 2-a] Benzimidazoles" Pakistan Journal of Scientific and Industrial Research 43 (2000) 168-170.

Pedro Molina et al. "Synthetic:Applications of C,C-Bis(Iminophosphoranes):Preparation of [5+5] Rigid Bicyclic Guanidines and 1,3,6-Benzothiadiazepino[3,2-a] benzimidazole Derivatives" Tetrahedron (1994) 10029-10036.

X. Wang et al. "Copper-Catalyzed Aerobic Oxidative Intramolecular C—H amination Leading to Imidazobenzimidazole Derivatives" Org. Lett. 14 (2012) 452-455.

Subramanian et al. "A Unified Strategy Towards N-Aryl Heterocycles by a One-Pot Copper-Catalyzed Oxidative C—H Amination of Azoles" Eur. J. Org. Chem. 2014, 5986-5997.

Guodong Yuan et al., "An efficient and facile synthesis of benzimidazo [1,2-a]benzimidazoles via copper-catalyzed domino addition/double cyclization" RSC Adv., 2014, 4, 21904.

Hubert, Andre J.; Reimlinger, Hans, "Thermolyse and Photolyse von Benzotriazolyl-(1)-Derivaten" Chemische Berichte 103 (1970) 2828-35.

*Primary Examiner* — Samantha L Shterengarts
(74) *Attorney, Agent, or Firm* — Riverside Law LLP

(57) ABSTRACT

The present invention relates to process for the preparation of a compound of formula (I), comprising heating a compound of formula (II) in the presence of a catalyst and a base in a solvent at elevated temperature. The compounds of formula (I) can be produced by the process easily, with excellent yield and purity and at low cost.

(I)

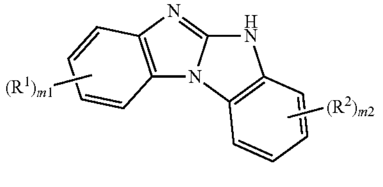

(II)

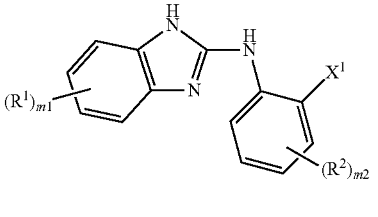

11 Claims, No Drawings

PROCESS FOR THE PREPARATION OF BENZIMIDAZO[1,2-A] BENZIMIDAZOLES

CROSS-REFERENCE TO RELATED APPLICATIONS

The present application is the U.S. national phase application filed under 35 U.S.C. § 371 claiming benefit to International Patent Application No. PCT/EP2016/067789, filed Jul. 26, 2016, which is entitled to priority under 35 U.S.C. § 119(a)-(d) to European Application No. 15178573.0, filed Jul. 28, 2015, all of which applications are incorporated herein by reference in their entireties.

The present invention relates to process for the preparation of a compound of formula (I), which can be produced by the process easily, with excellent yield and purity and at low cost.

Khan, Misbahul Ain; Ribeiro, Vera Lucia Teixeira, Pakistan Journal of Scientific and Industrial Research 43 (2000) 168-170 describes the synthesis of benzimidazo[1,2-a]benzimadozoles

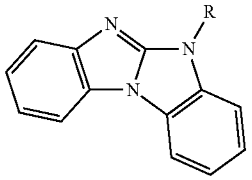

(R = H, Me, Et)

by trialkyl phosphite-induced deoxygenation and thermolysis of 1-(o-nitrophenyl)- and 1-(o-azidophenyl)benzimidazoles.

Pedro Molina et al. Tetrahedron (1994) 10029-10036 reports that aza Wittig-type reaction of bis(iminophosphoranes), derived from bis(2-aminophenyl)amine with two equivalents of isocyanate directly provided benzimidazo[1,2,a]benzimidazole derivatives.

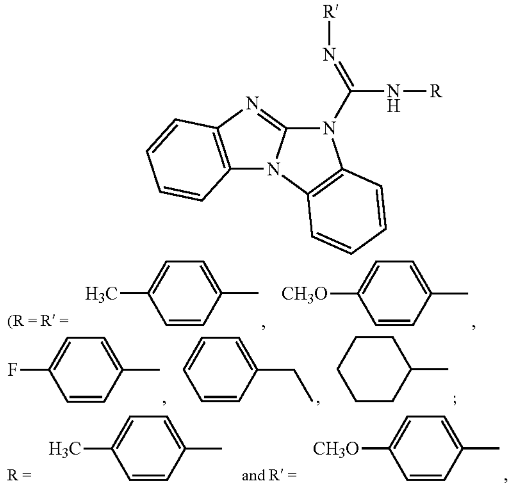

R = iso-propyl and R' = ethyl).

The synthesis of

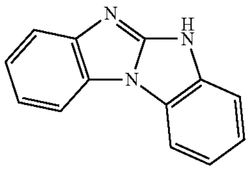 [SMILES: c1ccc2c(c1)nc1[nH]c3ccccc3n12]

is described, for example, in Achour, Reddouane; Zniber, Rachid, Bulletin des Societes Chimiques Belges 96 (1987) 787-92.

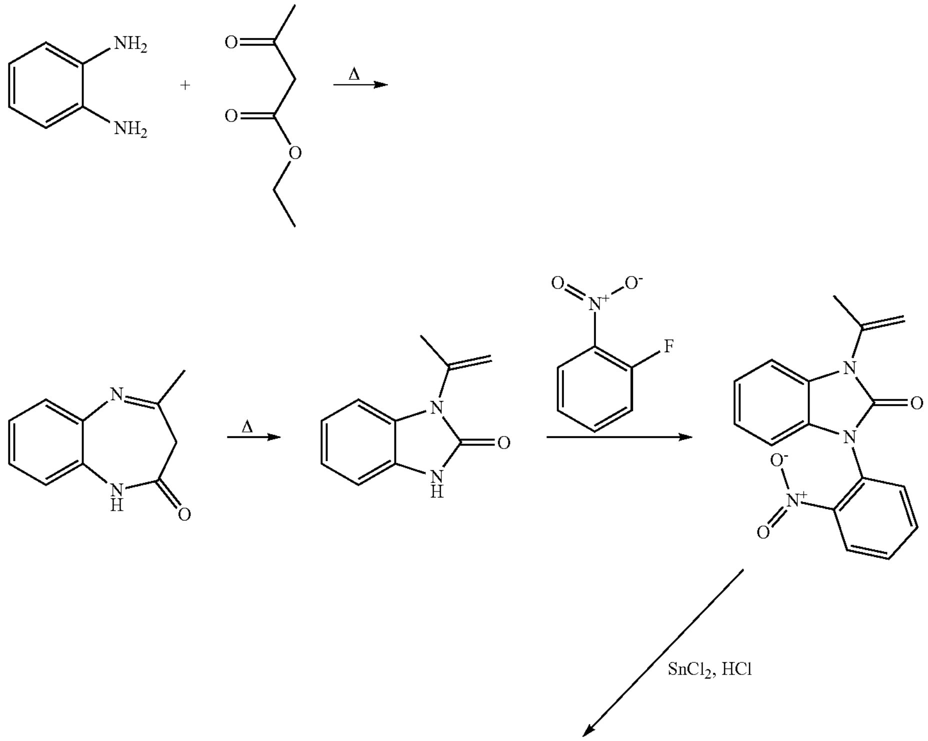

-continued

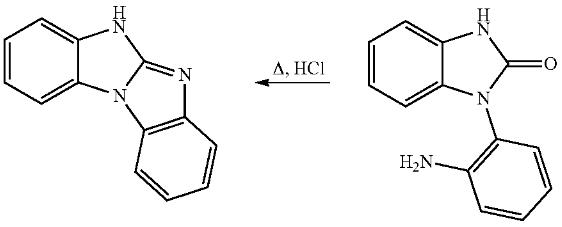

Hubert, Andre J.; Reimlinger, Hans, Chemische Berichte 103 (1970) 2828-35 describes the synthesis of benzimidazobenzimidazoles

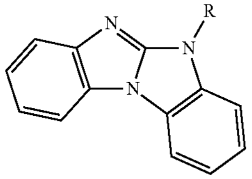

(R = H, $CH_3$, 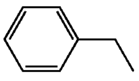).

X. Wang et al. Org. Lett. 14 (2012) 452-455 discloses a highly efficient copper-catalyzed synthesis for compounds of formula

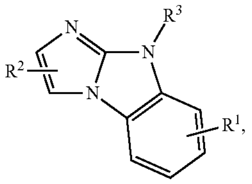

wherein compounds of formula

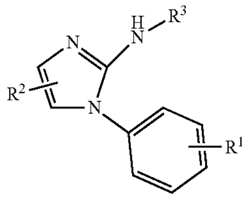

are reacted in the presence of copper acetate ($(Cu(OAc)_2)$/$PPh_3$/1,10-phenathroline/sodium acetate and oxygen in m-xylene (1 atm) at elevated temperature [published on web: Dec. 29, 2011].

In *Eur. J. Org. Chem.* 2014, 5986-5997 a new synthesis of benzimidazolo[1,2-a]benzimidazole is described.

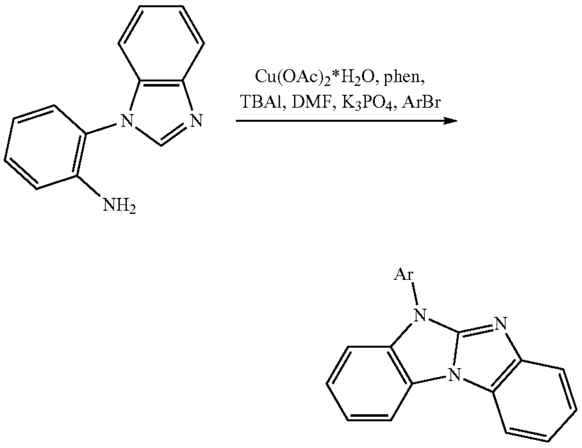

WO2012/130709 describes a process for the preparation of a compound of formula

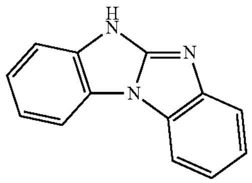
, which comprises heating a compound of formula

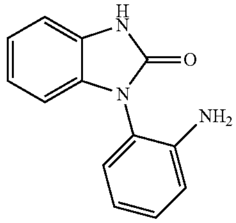 [SMILES: Nc1ccccc1-n1c(=O)[nH]c2ccccc21]

in $H_3PO_4$, polyphosporic acid, $CH_3SO_3H/P_2O_5$, $CH_3SO_3H$, or sulfuric acid. A solvent, or mixtures of solvents having a boiling point above 140° C., such as, for example, xylene, or mesitylen, may be present. The compound of formula

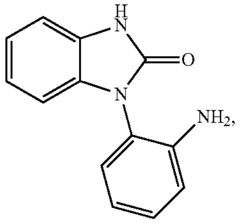 [SMILES: Nc1ccccc1-n1c(=O)[nH]c2ccccc21]

the preparation of which is described in Achour, Reddouane; Zniber, Rachid, Bulletin des Societes Chimiques Belges 96 (1987) 787-92, is stirred under an atmosphere of inert gas, such as, for example, nitrogen, or argon, at a temperature above 140° C., preferably above 160° C., more preferably above 180° C., for a time of 30 minutes to 3 weeks, preferably 1 to 48 h.

Guodong Yuan et al., RSC Adv., 2014, 4, 21904 disclose a copper-catalyzed synthesis of benzimidazo[1,2-a]benzimidazoles by domino addition/double cyclization of bis-(o-haloaryl) carbodiimides with primary amines. The proposed mechanism for the domino reaction of bis-(o-haloaryl)carbodiimide with primary amine is shown below:

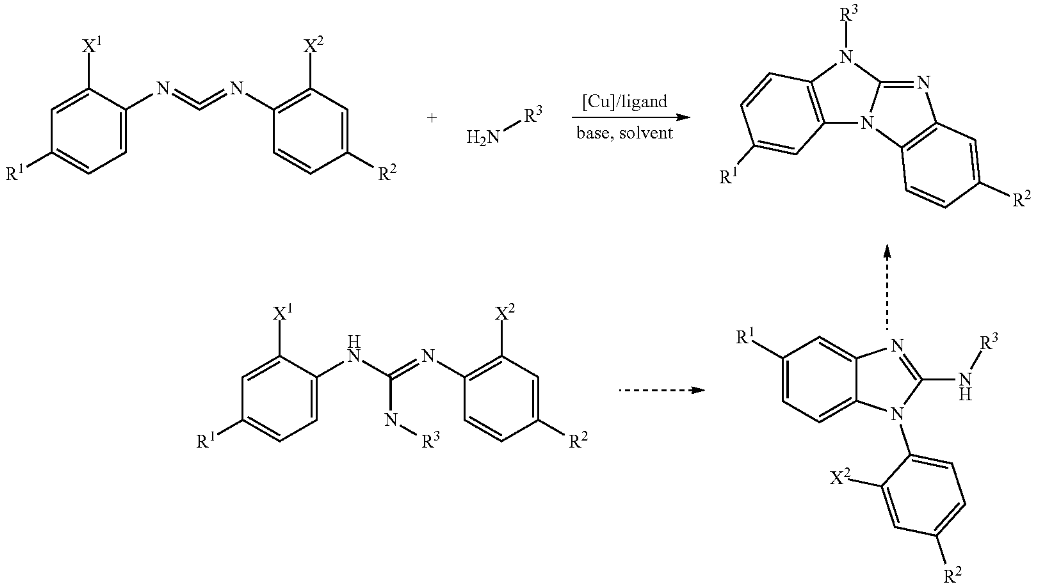

Compound 3s ($R^1$=H, $R^2$=F, $R^3$ is 2-(5methyl)pyridyl) is obtained with a yield of 80%.

I. V. Kolesnikova et al., Journal of Fluorine Chemistry, 40 (1988) 217-246 describes the Synthesis of polyfluorinated carbodiimides, chloroformamidines, guamidines and benzimidazoles. Among others the synthesis of 1,2,3,4,7,8,9,10-octafluoro-5-pentafluorophenyl-5H-benzimidazo[1,2-a] benzimidazole (XIII):

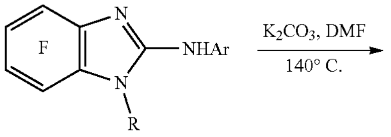

(XII)

-continued

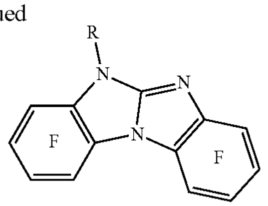

(XIII)

R = Ar = $C_6H_5$

Benzimidazo[1,2-a]benzimidazole derivatives and their use in electronic devices are, for example, described in WO2011/160757, WO2012/130709, WO2013/068376, WO2014/009317, WO2014/044722 and WO2015/014791.

A novel, concise and efficient method for the synthesis of benzimidazo[1,2-a]benzimidazoles has been developed. The starting materials are readily available, the application scope is broad, and the procedure is convenient.

Accordingly, the present invention relates to a process for the preparation of a compound of formula (I)

(I)

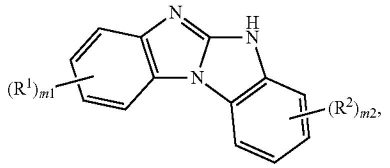

comprising:

a) heating a compound of formula (II)

(II)

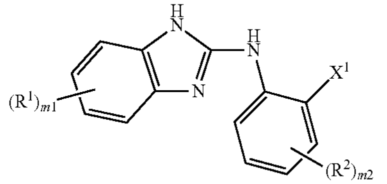

in the presence of a catalyst and a base in a solvent at elevated temperature, wherein m1 is 0, or an integer 1 to 4, m2 is 0, or an integer 1 to 4, $X^1$ is Cl, Br, or I, $R^1$ and $R^2$ are independently of each other a halogen atom, a $C_1$-$C_{25}$alkyl group, which can optionally be substituted by E and or interupted by D; a $C_1$-$C_{25}$alkoxy group, a group of formula $-(A^5)_v-(A^6)_s-(A^7)_t-(A^8)_u-R^{15}$, —$NR^{10}R^{11}$, or $Si(R^{12})(R^{13})(R^{14})$, v is 0, or 1, s is 0, or 1, t is 0, or 1, u is 0, or 1, $A^5$, $A^6$, $A^7$ and $A^8$ are independently of each other a $C_6$-$C_{24}$heteroarylen group, which can optionally be substituted by G, or a $C_2$-$C_{30}$heteroarylen group, which can optionally be substituted by G; wherein $R^{10}$ and $R^{11}$ are independently of each other a $C_6$-$C_{24}$aryl group, which can optionally be substituted by G; or a $C_2$-$C_{30}$heteroaryl group, which can optionally be substituted by G;

$R^{12}$, $R^{13}$ and $R^{14}$ are independently of each other a $C_1$-$C_{25}$alkyl group, which can optionally be substituted by E and or interupted by D; $C_6$-$C_{24}$aryl group, which can optionally be substituted by G; or a $C_2$-$C_{30}$heteroaryl group, which can optionally be substituted by G;

$R^{15}$ is a $C_6$-$C_{24}$aryl group, which can optionally be substituted by G; or a $C_2$-$C_{30}$heteroaryl group, which can optionally be substituted by G;

D is —S—, —SO—, —$SO_2$—, —O—, —$NR^{65}$—, —$SiR^{70}R^{71}$—, —$POR^{72}$—, —$CR^{63}$=$CR^{64}$—, or —C≡C—,

E is —$OR^{69}$, —$SR^{69}$, —$NR^{65}R^{66}$, —$CONR^{65}R^{66}$, or halogen,

G is E, or a $C_1$-$C_{18}$alkyl group, a $C_6$-$C_{24}$aryl group, a $C_6$-$C_{24}$aryl group, which is substituted by F, $C_1$-$C_{18}$alkyl, or $C_1$-$C_{18}$alkyl which is interrupted by O; a $C_2$-$C_{30}$heteroaryl group, or a $C_2$-$C_{30}$heteroaryl group, which is substituted by F, $C_1$-$C_{18}$alkyl, or $C_1$-$C_{18}$alkyl which is interrupted by O;

$R^{63}$ and $R^{64}$ are independently of each other H, $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl.

The compounds of formula (I) are intermediates in the production of compounds of formula (VI)

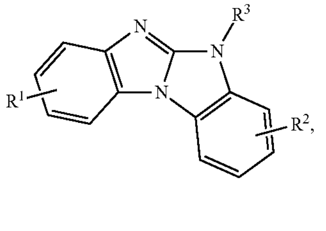

or

-continued (VIII)

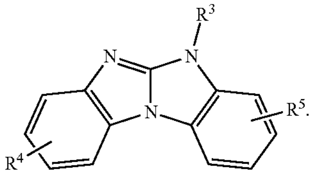

$R^4$ is a group of formula $-(A^5)_v-(A^6)_s-(A^7)_t-(A^8)_u-R^{15}$, —$Si(R^{12})(R^{13})(R^{14})$ or —$NR^{10}R^{11}$, $R^5$ has the meaning of $R^4$, or is H, and $R^3$ is a group of formula $-(A^1)_o-(A^2)_p-(A^3)_q-(A^4)_r-R^{16}$.

Compound of Formula (I)

$R^1$ and $R^2$ are independently of each other a halogen atom, a $C_1$-$C_{25}$alkyl group, which can optionally be substituted by E and or interupted by D; a $C_1$-$C_{25}$alkoxy group, a group of formula $-(A^5)_v-(A^6)_s-(A^7)_t-(A^8)_u-R^{15}$, —$NR^{10}R^{11}$, or $Si(R^{12})(R^{13})(R^{14})$, Halogen is fluorine, chlorine, bromine and iodine.

Examples of a group of formula $Si(R^{12})(R^{13})(R^{14})$ are a trimethylsilyl group, a triethylsilyl group, a tert-butyldimethylsilyl group, a propyldimethylsilyl group, a triisopropylsilyl group, a triphenylsilyl group, a phenyldimethylsilyl group, a t-butyldiphenylsilyl group, a tritolylsilyl group, a trixylylsilyl group, or a trinaphthylsilyl group.

Examples of the group $N(R^{10})(R^{11})$ include diphenylamino and a phenylnaphthylamino group.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methyl-heptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl.

$C_1$-$C_{25}$alkyl may be substituted by one or more E and/or interrupted by one or more units D. E is preferably —$OR^{69}$; —$SR^{69}$; —$NR^{65}R^{65}$; -or —$CONR^{65}R^{65}$, wherein $R^{65}$, $R^{67}$, $R^{68}$ and $R^{69}$ are independently of each other $C_1$-$C_{18}$alkyl, such as methyl, ethyl, n-propyl, iso-propyl, n-butyl, isobutyl, sec-butyl, hexyl, octyl, or 2-ethyl-hexyl, or $C_6$-$C_{14}$aryl, such as phenyl, tolyl, naphthyl, or biphenylyl. D is preferably —S—, —SO—, —$SO_2$—, —O—, —$NR^{65}$—, wherein $R^{65}$ is $C_1$-$C_{25}$alkyl, or $C_6$-$C_{14}$aryl, such as phenyl, tolyl, naphthyl, or biphenylyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy.

Examples of the groups $A^1$, $A^2$, $A^3$, $A^4$, $A^5$, $A^6$, $A^7$ and $A^8$ are a group of formula

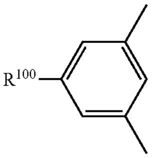, 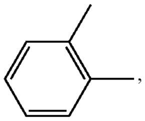, 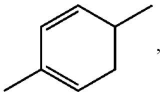,

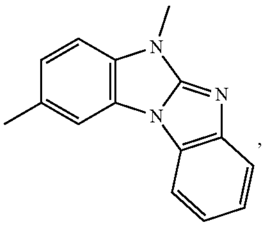, 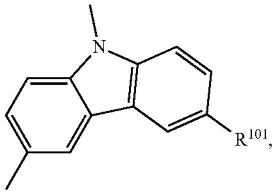,

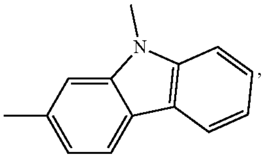, 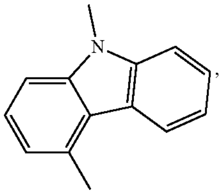,

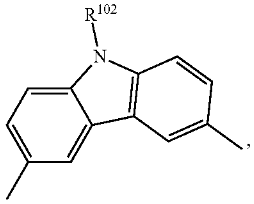, 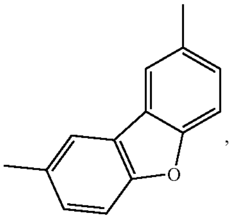,

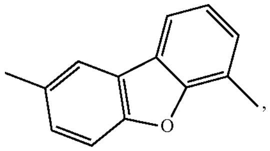, 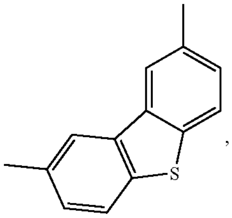, or

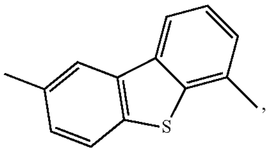, wherein $R^{100}$ is H, $Si(Ph)_3$, or

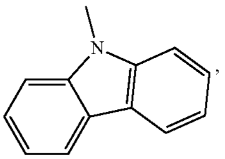, $R^{101}$ is H, or CN, $R^{102}$ is a phenyl group.

Examples of $R^{15}$ and $R^{16}$ are a group of formula

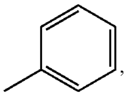, 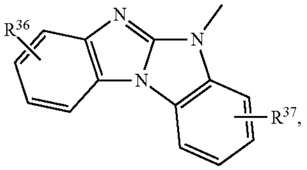,

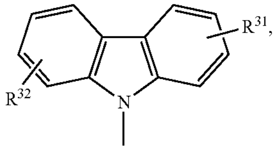 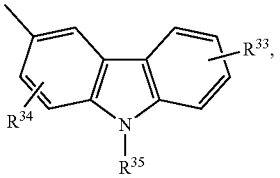

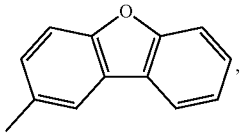, 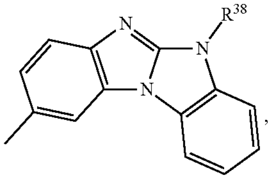,

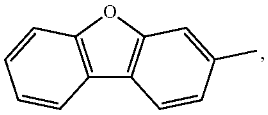, 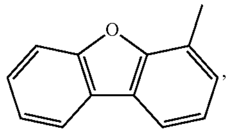,

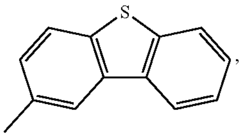, 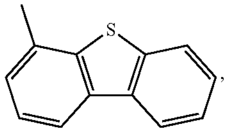,

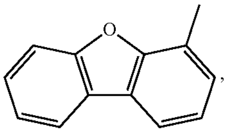, 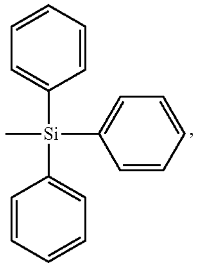,

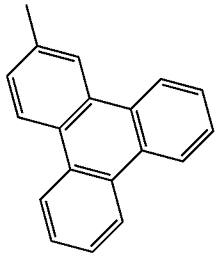 and 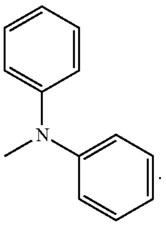.

$R^{31}$, $R^{32}$, $R^{33}$, $R^{34}$, $R^{36}$ and $R^{37}$ are independently of each other H, or a $C_1$-$C_{25}$alkyl group; $R^{35}$ and $R^{38}$ are independently of each a $C_6$-$C_{10}$aryl group, which can optionally be substituted by one, or more $C_1$-$C_{25}$alkyl groups.

The groups $R^{15}$ and $R^{16}$ may be substituted by G. G is preferably $C_1$-$C_{18}$alkyl, such as methyl, ethyl, n-propyl, iso-propyl, n-butyl, isobutyl, sec-butyl, hexyl, octyl, or 2-ethyl-hexyl; —$CF_3$, a $C_6$-$C_{14}$aryl group, a $C_6$-$C_{14}$aryl group, which is substituted by F, or $C_1$-$C_{18}$alkyl; a $C_2$-$C_{14}$heteroaryl group, or a $C_2$-$C_{14}$heteroaryl group, which is substituted by F, or $C_1$-$C_{18}$alkyl.

m1 and m2 are preferably, 0, 1, or 2, more preferably 0, or 1, most preferred 0.

If m1 is different from 0, $R^1$ is preferably $C_1$-$C_{25}$alkyl, $C_1$-$C_{25}$alkoxy, benzyloxy, Br, Cl, or F, more preferably $C_1$-$C_8$alkyl, $C_1$-$C_8$alkoxy, Br, Cl, or F.

If m2 is different from 0, $R^2$ is preferably $C_1$-$C_{25}$alkyl, $C_1$-$C_{25}$alkoxy, benzyloxy, Br, Cl, or F, more preferably $C_1$-$C_8$alkyl, $C_1$-$C_8$alkoxy, Br, Cl, or F.

The compound of formula (I) is preferably a compound of formula (Ia)

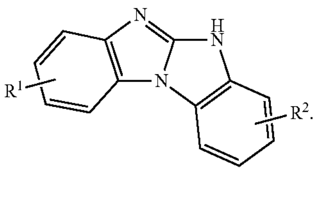

The compound of formula (II) is preferably a compound of formula (IIa)

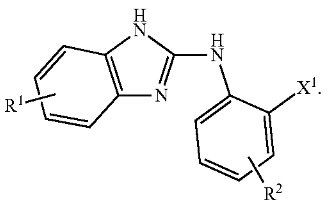

$X^1$ is preferably Cl, Br, or I, $R^1$ is preferably $C_1$-$C_8$alkyl, $C_1$-$C_8$alkoxy, Br, Cl, or F, and $R^2$ is preferably $C_1$-$C_8$alkyl, $C_1$-$C_8$alkoxy, Br, Cl, or F.

Most preferred the compound of formula (I) is a compound of formula (I-1)

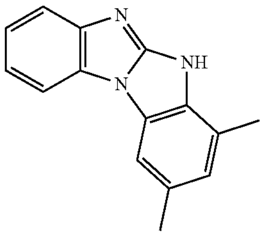

, (I-2)

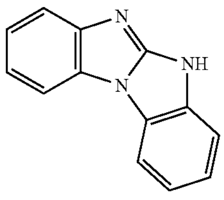

, (I-3)

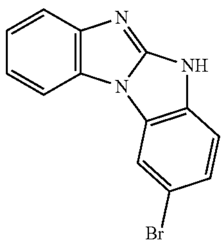

,

-continued (I-4)

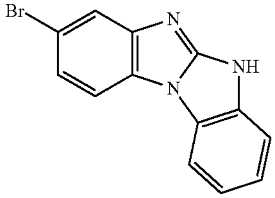

, (I-5)

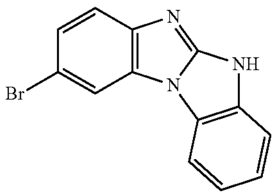

, (I-6)

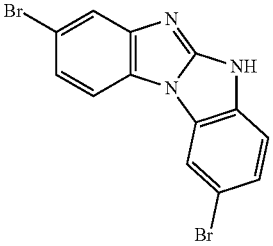

and (I-7)

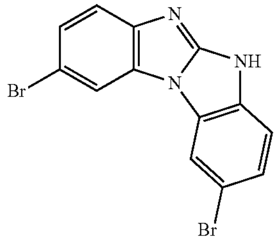

.

The, at present, most preferred compound of formula (I) is compound (I-2).

Catalyst:

The catalyst is preferably a Cu(0) powder, especially a Cu(I) salt, or a Cu(II) salt.

Preferred Cu(I) salts are selected from CuCl, CuBr, CuI, CuBr—$SMe_2$, CuSCN, and CuOTf (Cupric trifluoromethane sulfonate). More preferably, the Cu(I) catalyst is selected from CuCl, CuBr, and CuI.

Preferred Cu(II) salts are selected from $CuBr_2$, $CuCO_3$, $Cu(OAc)_2$, and $Cu(OTf)_2$.

The amount of Cu, especially Cu(I) and Cu(II) catalyst used depend on the selected starting materials and reaction conditions. Preferably, from 0.01 to 0.20 equivalents of Cu(I) or Cu(II) catalyst are present.

A ligand may be added for performing the coupling reaction. Examples of ligands used in the Ullmann-coupling reaction would be known to a person of ordinary skill in the art, and can include, without limitation, dimethylethylenediame (DMEDA), tetramethylethylenediamine (TMED), 2,2'-dipyridyl (DPD), triphenylphosphine (TPP), N,N-dimethylglycine (NDMG), tri-t-butylphosphine (tri-tBuP), N-methylglycine, 2,2,4,4-tetramethyl-3,5-heptanedione (TMHD), 8-hydroxyquinoline (HQL), and 1,10-phenanthroline (PNT).

The amount of ligand present should be approximately equivalent to the amount of Cu catalyst present.

In a particularly preferred embodiment the catalyst is selected from CuI, and $CuBr_2$ and the catalyst comprises optionally a ligand, especially DMEDA.

In the most preferred embodiment the catalyst is selected from CuI, and $CuBr_2$ and comprises no ligand.

Base:

Preferably this base is inorganic and more preferably weak. Though there is no particular limitation, there can be used, for example, alkali metal carbonates, alkali metal hydrogencarbonates, alkali metal phosphates, alkali metal hydrogenphosphates and alkali metal dihydrogenphosphates. As the alkali metal carbonates, there can be exemplified sodium carbonate, lithium carbonate, cesium carbonate and potassium carbonate. As the alkali metal phosphates, there can be exemplified sodium phosphate, potassium phosphate, cesium phosphate and lithium phosphate. The alkali metal carbonates, especially $K_2CO_3$ and $Cs_2CO_3$, are more preferred. Potassium carbonate is preferred when a polar, aprotic solvent is used. Caesium carbonate is preferred if a less polar organic solvent is used.

The amount of base is preferably 1.0 to 2.0 molar equivalents, more preferably 1.0 to 1.5 equivalents.

Solvent:

Preferably, the Ullmann coupling is performed in a suitable polar solvent, or a mixture of suitable polar solvents, which are stable under basic conditions. Suitable polar solvents include, but are not limited to, ether and aprotic solvents. Suitable ether solvents include: 1,2-dimethoxyethane (DME), 1,2-diethoxyethane (DEE), tetrahydrofuran, 1,3-dioxane, 1,4-dioxane, furan, ethylene glycol dimethyl ether, ethylene glycol diethyl ether, diethylene glycol dimethyl ether, diethylene glycol diethyl ether, triethylene glycol dimethyl ether, or t-butyl methyl ether. Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), N-methylacetamide, N,N-dimethylacetamide (DMA), N-methylformamide, dimethyl sulfoxide, propionitrile, ethyl formate, hexachloroacetone, sulfolane, N,N-dimethylpropionamide, tetramethylurea, nitromethane, nitrobenzene, or hexamethylphosphoramide.

Most preferred, the solvent is a solvent which is miscible with water, such as, for example, dimethoxymethane (DME), diethoxyethane (DEE), 1,3-dioxane, 1,4-dioxane, N-methyl-pyrrolidinone (NMP), N,N-dimethylacetamide (DMA), dimethylformamide (DMF) and mixtures of these solvents.

The Ullmann coupling of is a thermally promoted reaction. Thus, it is preferable to run the coupling reaction under heat. Preferably, the contacting is performed at a temperature of from 100° C. to reflux of the solvent and the reaction is run from 4 to 24 hours.

Compounds of formula (II) may be obtained by reacting a compound of formula (III)

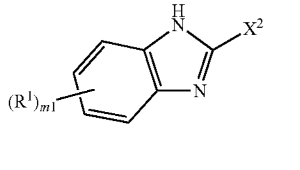

with a compound of formula (IV)

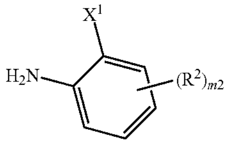

in the presence of an acid in a solvent at elevated temperature, wherein $X^2$ is Cl, Br, or I, especially Cl, and m1, m2, $R^1$, $R^2$ and $X^1$ are defined above.

It is preferable to run the coupling reaction of compound (III) and (IV) under heat. Preferably, the contacting is performed at a temperature of from 100° C. to reflux of the solvent and the reaction is run from 4 to 24 hours.

Acid:

The acids include inorganic acids, such as, for example, hydrochloric acid, hydrobromic acid, sulfuric acid, nitric acid, and phosphoric acid, preferably hydrochloric acid, and sulfuric acid, and organic acids, such as, for example, methane sulfonic acid, campher sulfonic acid, p-toluene sulfonic acid, preferably methane sulfonic acid, campher sulfonic acid, p-toluene sulfonic acid.

The amount of acid is preferably 1.0 to 2.0 molar equivalents, more preferably 1.0 to 1.5 equivalents.

Solvent:

In principal, step a) can be performed in a suitable aromatic solvent such as, for example, toluene and xylene. Preferably, step a) is performed in a suitable polar solvent, or a mixture of suitable polar solvents, which are stable against acids. Suitable polar solvents include, but are not limited to aprotic solvents. Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), N-methylacetamide, N,N-dimethylacetamide (DMA), N-methylformamide, dimethyl sulfoxide, propionitrile, ethyl formate, hexachloroacetone, sulfolane, N,N-dimethylpropionamide, tetramethylurea, nitromethane, nitrobenzene, or hexamethylphosphoramide.

Most preferred, the solvent is a solvent which is miscible with water, such as, for example, dimethoxymethane (DME), diethoxyethane (DEE), 1,3-dioxane, 1,4-dioxane, N-methylpyrrolidinone (NMP), N,N-dimethylacetamide (DMA), dimethylformamide (DMF) and mixtures of these solvents.

The compounds of formula (IV) are commercially available, or can be produced according to methods known to the person skilled in the art.

Examples of commercially available compounds of formula (IV) are shown below:

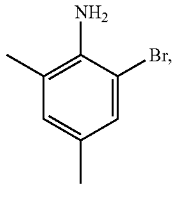

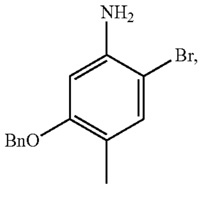

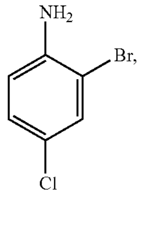

-continued

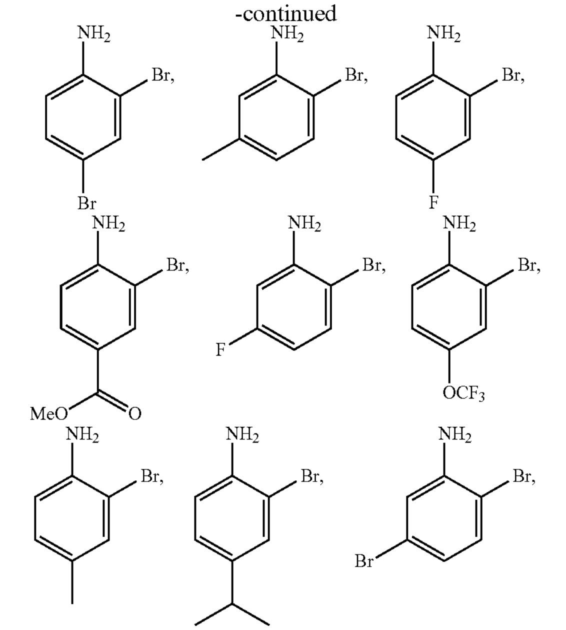

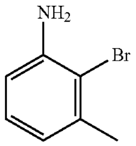

and

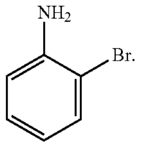

(Bn = benzyl)

The compounds of formula (III) are commercially available, or can be produced according to methods known to the person skilled in the art.

Examples of commercially available compounds of formula (III) are shown below:

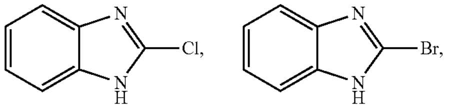

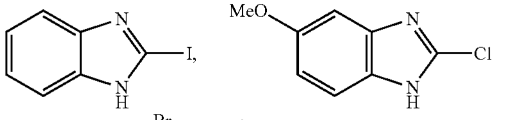

and

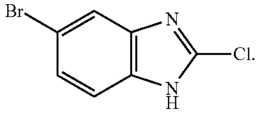

The process of the present invention is illustrated in more detail on basis of the synthesis of 6H-benzimidazolo[1,2-a] benzimidazole, but is not limited thereto.

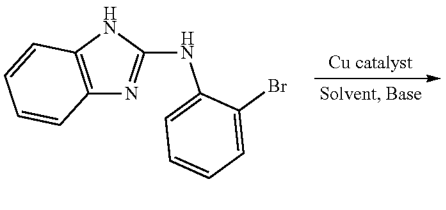

-continued

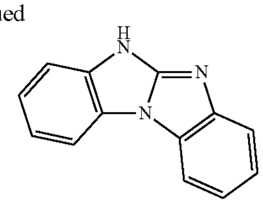

The Cu catalyst is preferably CuI, or $CuBr_2$.

The solvent is preferably 1,4-dioxane, DMF, DMA, NMP, or a mixture of these solvents. Most preferred are DMF, DMA, or NMP. Preferably, from 0.01 to 0.20 equivalents of Cu(I) or Cu(II) catalyst are present.

The base is preferably $K_2CO_3$, or $CsCO_3$. The amount of base is preferably 1.0 to 2.0 molar equivalents, more preferably 1.0 to 1.5 equivalents.

The solvent is preferably a solvent which is miscible with water, such as, for example, 1,3-dioxane, 1,4-dioxane, NMP, DMA, DMF and mixtures of these solvents.

Preferably, the Ullmann coupling is performed at a temperature of from 100° C. to reflux of the solvent and the reaction is run from 4 to 24 hours.

The currently best results are obtained, when the Ullmann coupling is done in DMF at a temperature of about 130° C. in the presence of a catalytic amount of CuI, or $CuBr_2$ and an excess of caesium carbonate. Under these conditions, cyclization is complete within 4 h, proceeds quantitatively and yields reasonably pure material (HPLC ca. 95 area-%) after precipitation by adding water.

The purity of the crude product can be raised from ca. 95 to above 97.7% by recrystallization in DMF, DMA, or NMP.

The crude reaction product contains significant amounts of Cu salts. The amount of Cu salts can be decreased by a factor of 2 by reducing the amount of Cu catalyst ($CuBr_2$) from 5 to 2.0 or even 1.0 equivalents.

The copper content can be further decreased to a level of below 500 ppm and the purity of the product can be increased to more than 99%, when the crude reaction product is recrystallized in boiling acetic acid.

The required precursor, N-(2-bromophenyl)-1H-benzimidazol-2-amine, can be obtained by reacting 2-chlorobenzimidazole with 2-bromo aniline.

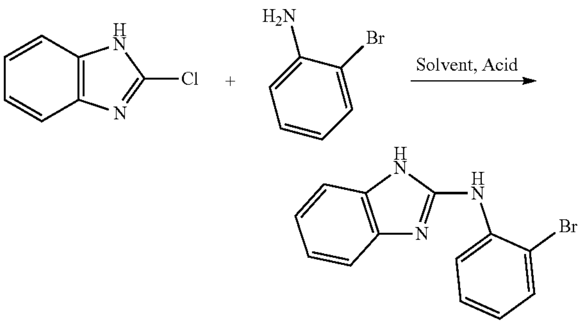

The currently best results are obtained by reacting 2-chlorobenzimidazole with o-bromoaniline in NMP at a temperature of about 100° C. in the presence of a stoichiometric amount of methanesulfonic acid. Complete conversion is achieved after 6 h. After dilution with water and neutralization with aqueous sodium hydroxide, the precipitated reaction product can be isolated by filtration at room temperature.

Benzimidazo[1,2-a]benzimidazole derivatives of formula (I) can be used in electronic devices and/or are starting materials and/or intermediates in the synthesis of materials which can be used in electronic devices. Reference is made, for example, to WO2011/160757, WO2012/130709 (compounds A-1 to A-32, B-1 to B-35, C-1 to C-78, F-1 to F-62, G-1 to G-62), WO2013/068376 (compounds A-1 to A-18, B-1 to B-18, C-1 to C-18, D-1 to D-19, E-1 to E-6), WO2014/009317 (compounds A-1 to A-51) and WO2014/044722 (A-1 to A-65, B-1 to B-8, C-1 to C-65, D-1 to D-8, E-1 to E-65, or F-1 to F-65) and WO2015/014791.

Accordingly, the process of the present invention can further comprise reacting c1)

(Ia)

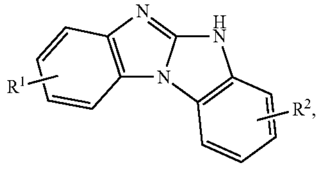

with a compound of formula $R^3—X^3$ (V), to obtain a compound of formula (VI)

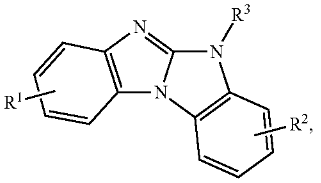

wherein $X^3$ is Cl, Br, or I, $R^3$ is a group of formula $-(A^1)_o-(A^2)_p-(A^3)_q-(A^4)_r-R^{16}$, o is 0, or 1, p is 0, or 1, q is 0, or 1, r is 0, or 1, $A^1$, $A^2$, $A^3$ and $A^4$ are independently of each other a $C_6$-$C_{24}$arylen group, which can optionally be substituted by G, or a $C_2$-$C_{30}$heteroarylen group, which can optionally be substituted by G;

$R^{16}$ is a $C_6$-$C_{24}$aryl group, which can optionally be substituted by G; or a $C_2$-$C_{30}$heteroaryl group, which can optionally be substituted by G; and $R^1$, $R^2$ and G are defined above.

The bromination of 5-phenylbenzimidazolo[1,2-a]benzimidazole can be carried out in analogy to the bromination of carbazole, which is, for example, described in J. Mater. Chem. 18 (2008) 1296-1301.

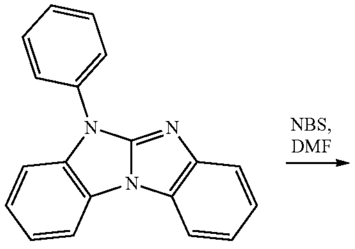

-continued

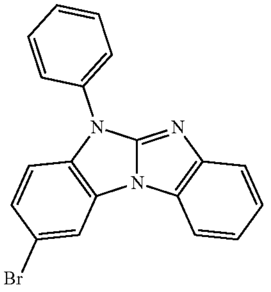

Other bromination methods are, for example, described in Helvetica Chimica Acta 89 (2006) 1123 and SYNLETT 17 (2006) 2841-2845.

Halogenation agents for the selective halogenation of benzimidazo[1,2-a]benzimidazole derivatives of formula (I) are available. Examples are N-chlorosuccinimide (NCS) (Synlett 18 (2005) 2837-2842); $Br_2$ (Synthesis 10 (2005) 1619-1624), N-bromosuccinimide (NBS) (Organic Letters 12 (2010) 2194-2197; Synlett (2006) 2841-2845), 1,3-dibromo-5,5-dimethylhydantoin (DBH) (Organic Process Research & Development 10 (2006) 822-828, US2002/0151456), $CuBr_2$ (Synthetic Communications 37 (2007) 1381-1388); $R_4NBr_3$ (Can. J. Chem. 67 (1989) 2062), N-iodosuccinimide (NIS) (Synthesis 12 (2001) 1794-1799, J. Heterocyclic Chem. 39 (2002) 933), $KI/KIO_3$ (Org. Lett. 9 (2007) 797, Macromolecules 44 (2011) 1405-1413), $NaIO_4/I_2/H_2SO_4$ or $NaIO_4/KI/H_2SO_4$ (J. Heterocyclic Chem. 38 (2001) 77; J. Org. Chem. 75 (2010) 2578-2588); iodine monochloride (ICl; Synthesis (2008) 221-224). Additional methods are described in J. Org. Chem. 74 (2009) 3341-3349; J. Org. Chem. 71 (2006) 7422-7432, Eur. J. Org. Chem. (2008) 1065-1071, Chem. Asian J. 5 (2010) 2162-2167, Synthetic. Commun. 28 (1998) 3225.

Accordingly, the compound of formula (VI)

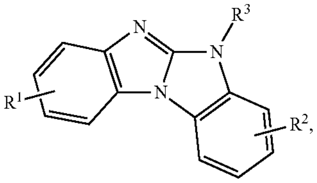

wherein $R^1$ and $R^2$ are H, is halogenated to obtain a compound of formula (VII)

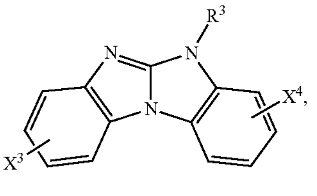

wherein $X^3$ is Br, or I and $X^4$ is H, Br, or I and $R^3$ is defined above.

The compound of formula

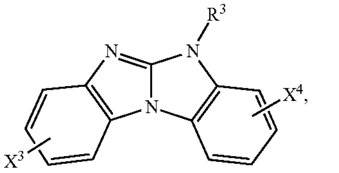

(VII)

wherein $X^3$ is Br, or I and $X^4$ is H, Br, or I, is transformed to a compound of formula

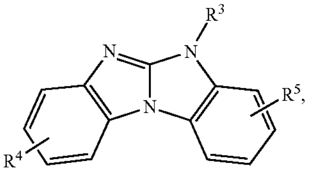

(VIII)

by known methods, wherein $R^3$ is defined above, $R^4$ is a group of formula $-(A^5)_v-(A^6)_s-(A^7)_t-(A^8)_u-R^{15}$, $—Si(R^{12})(R^{13})(R^{14})$ or $—NR^{10}R^{11}$, $R^5$ has the meaning of $R^4$, or is H, v, s, t, u, $A^5$, $A^6$, $A^7$, $A^8$, $R^{10}$, $R^{11}$, $R^{12}$, $R^{13}$ and $R^{14}$ are defined above;

$R^{15}$ is a group of formula

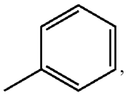,
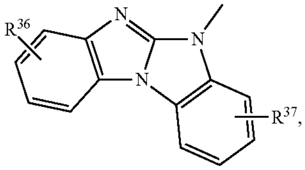
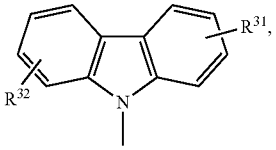
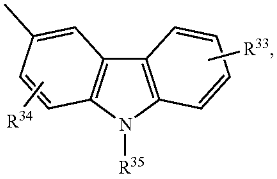
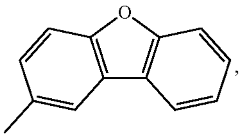,
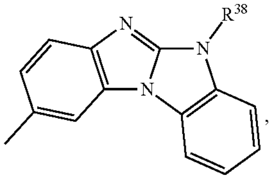,
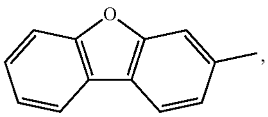,
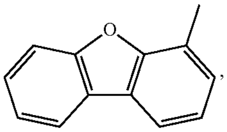,
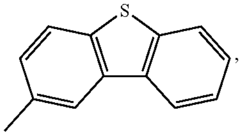,
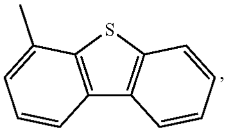, -continued

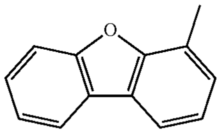,
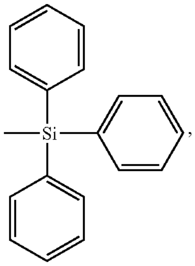,
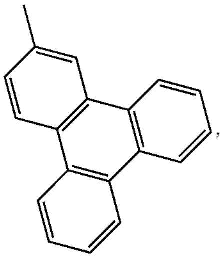, or
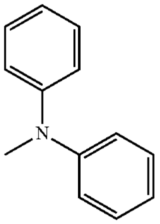

$R^{31}$, $R^{32}$, $R^{33}$, $R^{34}$, $R^{36}$ and $R^{37}$ are independently of each other H, or a $C_1$-$C_{25}$alkyl group; $R^{35}$ and $R^{38}$ are independently of each a $C_6$-$C_{10}$aryl group, which can optionally be substituted by one, or more $C_1$-$C_{25}$alkyl groups.

Heteroarylation can be effected, for example, by copper-catalyzed coupling of

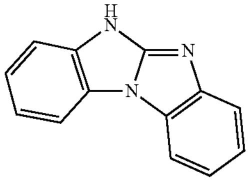 [SMILES: c1ccc2c(c1)nc1[nH]c3ccccc3n12]

to a halogenated compound of the formula

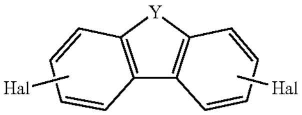

(Ullmann reaction, Y is O, S, or $NY^1$, wherein $Y^1$ is, for example,

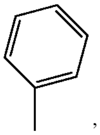,
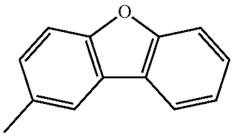,
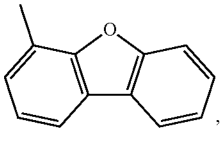, Hal = Cl, Br, or I).

5-phenylbenzimidazolo[1,2-a]benzimidazole can be prepared according to example 2a) of WO2014/009317:

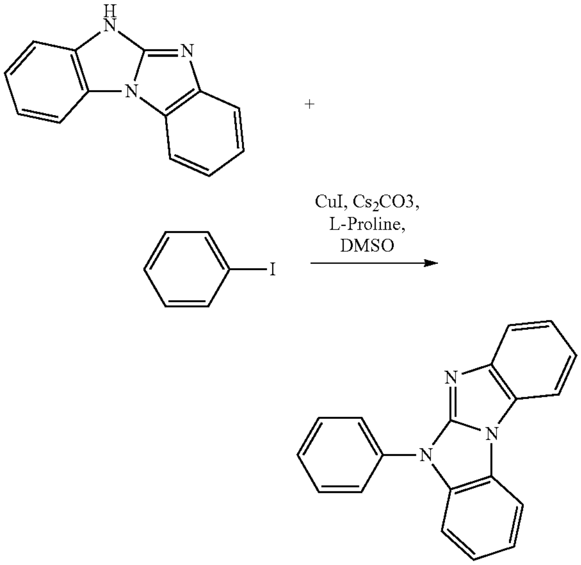
2-bromo-5-phenyl-benzimidazolo[1,2-a]benzimidazole can be prepared according to example 2a) of WO2014/009317:
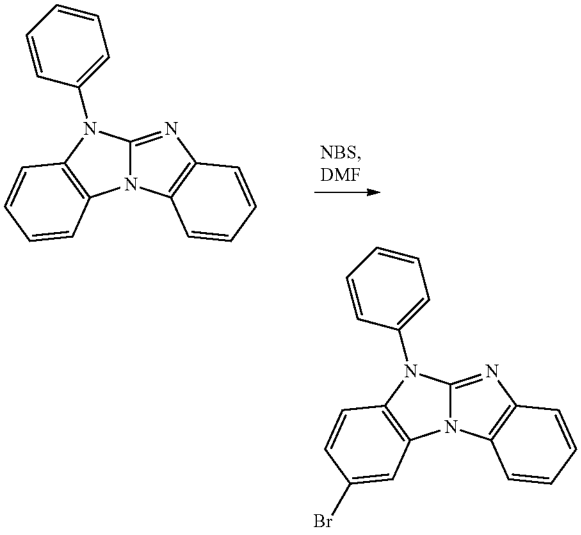
2-iodo-5-phenyl-benzimidazolo[1,2-a]benzimidazole can be prepared according to example 4a) of WO2014/009317:
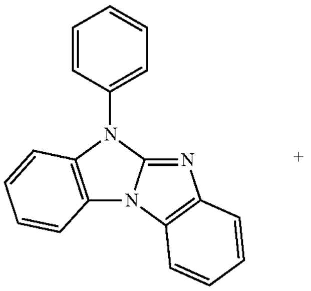
-continued
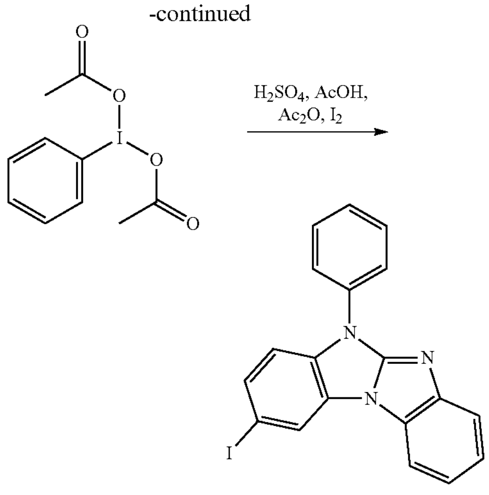
2-Iodo-5-phenyl-benzimidazolo[1,2-a]benzimidazole can be reacted with carbazole to yield compound (A-24). Reference is made to example 4b) of WO2014/009317.
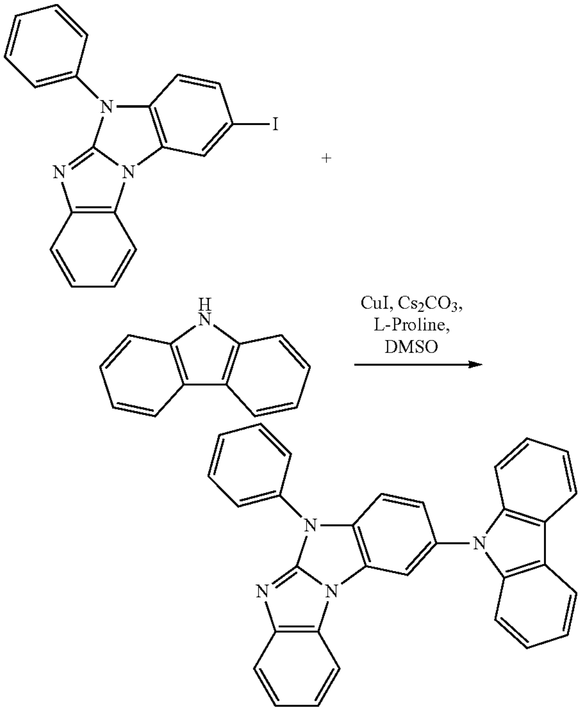
A-24
Compounds of formula
(X)
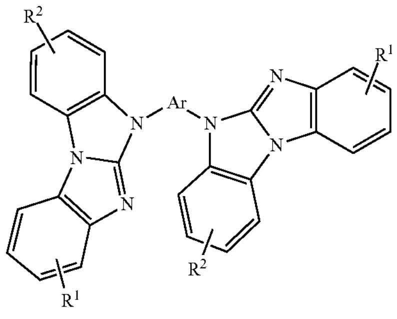

can be obtained by reacting c2) a compound of formula

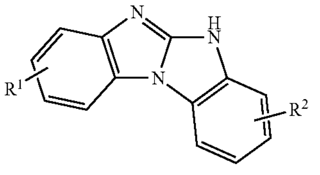

(I)

with a compound of formula $X^5$—Ar—$X^6$ (IX). $X^5$ and $X^6$ are independently of each other Cl, Br, or I, Ar is an (hetero)aromatic divalent linking group and $R^1$ and $R^2$ are defined above.

The following examples are included for illustrative purposes only and do not limit the scope of the claims. Unless otherwise stated, all parts and percentages are by weight.

EXAMPLES

Example 1 a) Synthesis of N-(2-bromophenyl)-1H-benzimidazol-2-amine

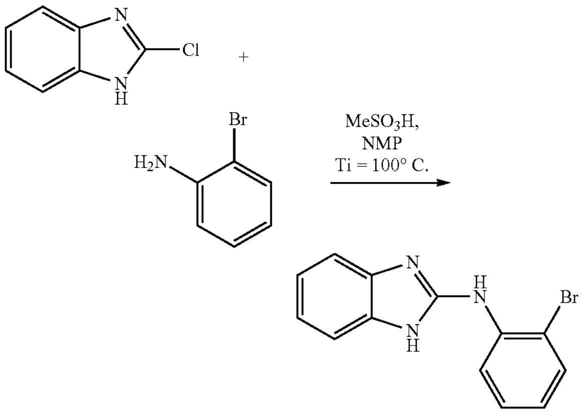

2-Chlorobenzimidazole (325.0 g, 2.13 mol) and 2-bromoaniline (403.1, 2.34 mol) are dissolved in NMP (1065 mL) at 20° C. Methanesulfonic acid (225.2 g, 2.34 mL) is added dropwise over ca. 0.5 h. The resulting suspension is heated to 100° C. and stirred until complete conversion of 2-chlorobenzimidazole. The reaction mixture is then cooled to 20° C., diluted with water (650 mL) and neutralized with 30 w-% aqueous sodium hydroxide (596.4 g, 4.47 mol). The precipitated reaction product is isolated by filtration, washed with water and dried under vacuum at 90° C. N-(2-bromophenyl)-1H-benzimidazol-2-amine (558.6 g, 91%) is obtained as an off-white amorphous solid, which is used without purification in the ring closure step.

$^1$H-NMR (DMSO-d6): δ=6.93 (dt, J=1.1, 7.9 Hz, 1H), 6.99-7.06 (m, 2H), 7.34-7.44 (m, 3H), 7.63 (dd, J=1.4, 8.0 Hz, 1H), 8.48 (brs, 1H), 8.68 (dd, J=0.6, 8.1 Hz, 1H), 11.19 (brs, 1H) ppm.

b) Synthesis of 6H-benzimidazolo[1,2-a]benzimidazole (I-2)

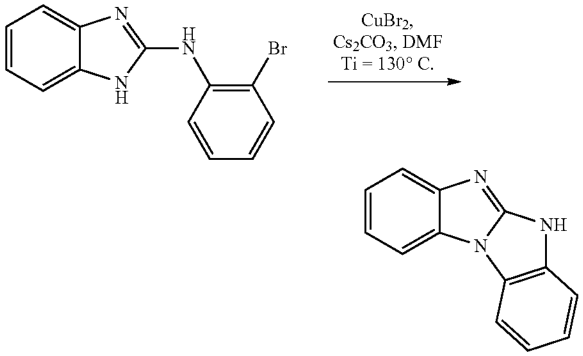

N-(2-bromophenyl)-1H-benzimidazol-2-amine 350.0 g, 1.21 mol), cesium carbonate (593.6 g, 1.82 mol) and copper (II) bromide (5.43 g, 0.024 mol) are suspended in DMF (1225 mL). The resulting suspension is heated to 130° C. and stirred until complete conversion of N-(2-bromophenyl)-1H-benzimidazol-2-amine. The reaction mixture is then cooled to 20° C. and diluted with water. The precipitated reaction product is isolated by filtration, washed thoroughly with water and dried under vacuum at 100° C. 6H-benzimidazolo[1,2-a]benzimidazole (243.4 g, 97%) is obtained as an off-white amorphous solid.

$^1$H-NMR (DMSO-d6): δ=7.23 (dt, J=0.8, 7.6 Hz, 2H) 7.30 (dt, J=0.8, 7.6 Hz, 2H), 7.50 (d, J=7.6 Hz, 2H), 8.09 (d, J=7.6 Hz, 2H), 12.03 (brs, 1H) ppm. $^{13}$C-NMR (DMSO-d6): δ=111.2, 115.0, 120.3, 123.3, 126.6, 141.6, 153.8 ppm.

Example 2 a) Synthesis of N-(2-bromophenyl)-1H-benzimidazol-2-amine

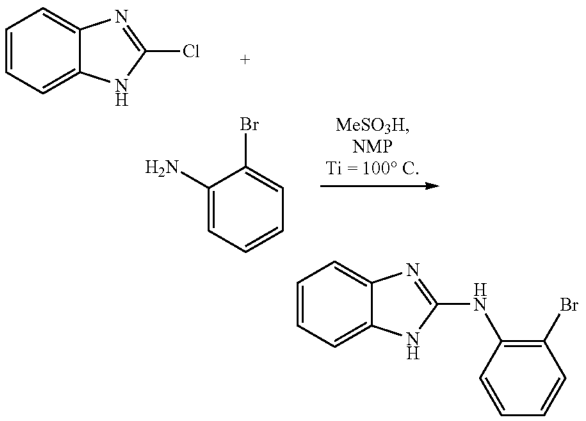

2-Chlorobenzimidazole (325.0 g, 2.13 mol) and 2-bromoaniline (403.1 g, 2.34 mol) are dissolved in NMP (1065 mL) at 20° C. Methanesulfonic acid (225.2 g, 2.34 mL) is added dropwise over ca. 0.5 h. The resulting suspension is heated to 100° C. and stirred until complete conversion of 2-chlorobenzimidazole. The reaction mixture is then cooled to 20° C., diluted with water (650 mL) and neutralized with 30 w-% aqueous sodium hydroxide (596.4 g, 4.47 mol). The precipitated reaction product is isolated by filtration, washed with water and dried under vacuum at 90° C. N-(2-bromophenyl)-1H-benzimidazol-2-amine (558.6 g, 91%) is obtained as an off-white amorphous solid, which was used without purification in the ring closure step.

1H-NMR (DMSO-d6): δ=6.93 (dt, J=1.1, 7.9 Hz, 1H), 6.99-7.06 (m, 2H), 7.34-7.44 (m, 3H), 7.63 (dd, J=1.4, 8.0 Hz, 1H), 8.48 (brs, 1H), 8.68 (dd, J=0.6, 8.1 Hz, 1H), 11.19 (brs, 1H) ppm.

b) Synthesis of 6H-benzimidazolo[1,2-a]benzimidazole (I-2)

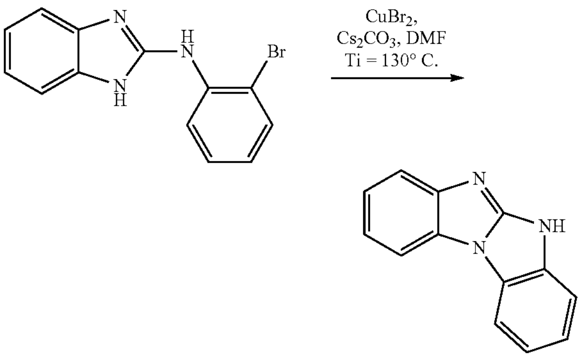

N-(2-bromophenyl)-1H-benzimidazol-2-amine (350.0 g, 1.21 mol), cesium carbonate (593.6 g, 1.82 mol) and copper (II) bromide (5.43 g, 0.024 mol) are suspended in DMF (1225 mL). The resulting suspension is heated to 130° C. and stirred until complete conversion of N-(2-bromophenyl)-1H-benzimidazol-2-amine. The reaction mixture is then cooled to 20° C. and diluted with water. The precipitated reaction product is isolated by filtration, washed thoroughly with water and dried under vacuum at 100° C. 6H-benzimidazolo[1,2-a]benzimidazole (243.4 g, 97%) is obtained as an off-white amorphous solid, which is further purified by recrystallization from acetic acid.

1H-NMR (DMSO-d6): δ=7.23 (dt, J=0.8, 7.6 Hz, 2H), 7.30 (dt, J=0.8, 7.6 Hz, 2H), 7.50 (d, J=7.6 Hz, 2H), 8.09 (d, J=7.6 Hz, 2H), 12.03 (brs, 1H) ppm. 13C-NMR (DMSO-d6): δ=111.2, 115.0, 120.3, 123.3, 126.6, 141.6, 153.8 ppm.

Example 3 a) Synthesis of N-(2-bromo-4,6-dimethyl-phenyl)-1H-benzimidazol-2-amine

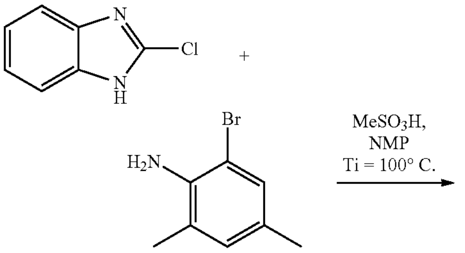

-continued

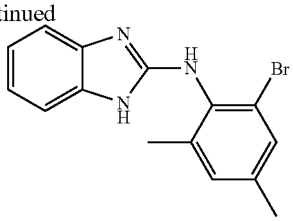

2-Chlorobenzimidazole (6.9 g, 45.4 mmol) and 2-bromo-4,6-dimethylaniline (10.0 g, 50.0 mmol) are dissolved in NMP (23 mL) at 20° C. Methanesulfonic acid (4.8 g, 50.0 mmol) is added dropwise over ca. 0.5 h. The resulting suspension is heated to 100° C. and stirred until complete conversion of 2-chlorobenzimidazole. The reaction mixture is then cooled to 20° C., diluted with water (14 mL) and neutralized with 30 w-% aqueous sodium hydroxide (12.7 g, 95.3 mmol). The precipitated reaction product is isolated by filtration, washed with water and dried under vacuum at 90° C. Crude N-(2-bromo-4,6-dimethyl-phenyl)-1H-benzimidazol-2-amine (10.3 g, 72%) is obtained as an off-white amorphous solid, which was further purified by recrystallization from methanol.

1H-NMR (DMSO-d6): δ=2.21 (s, 3H), 2.31 (s, 3H), 6.83-6.95 (m, 2H), 7.06-7.18 (m, 3H), 7.39 (brs, 1H), 8.58 (brs, 1H), 10.75 (brs, 1H) ppm.

b) Synthesis of 2,4-dimethyl-5H-benzimidazolo[1,2-a]benzimidazole (I-1)

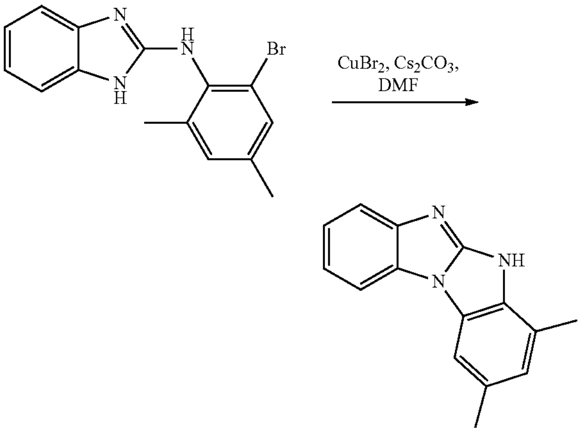

N-(2-bromo-4,6-dimethyl-phenyl)-1H-benzimidazol-2-amine (5.8 g, 18.2 mmol), cesium carbonate (8.9 g, 27.3 mmol) and copper(II) bromide (81.2 mg, 0.36 mmol) are suspended in DMF (18 mL). The resulting suspension is heated to 130° C. and stirred until complete conversion of N-(2-bromo-4,6-dimethyl-phenyl)-1H-benzimidazol-2-amine. The reaction mixture is then cooled to 20° C. and diluted with water. The precipitated reaction product is isolated by filtration, washed thoroughly with water and dried under vacuum at 100° C. Crude 2,4-dimethyl-5H-benzimidazolo[1,2-a]benzimidazole (3.9 g, 91%) is obtained as an off-white amorphous solid, which was further purified by recrystallization from acetic acid.

1H-NMR (DMSO-d6): δ=2.46 (s, 3H), 2.48 (s, 3H), 6.95 (brs, 1H), 7.20 (dt, J=1.0, 7.7 Hz, 1H), 7.27 (dt, J=1.0, 7.6 Hz, 1H), 7.51 (d, J=7.8 Hz, 1H), 7.74 (brs, 1H), 8.04 (d, J=7.6 Hz, 1H), 11.85 (brs, 1H) ppm. 13C-NMR (DMSO-d6): δ=17.0, 21.5, 109.0, 111.0, 115.6, 119.9, 123.1, 123.4, 125.3, 126.0, 127.0, 129.8, 136.9 (brs), 143.3 (brs), 153.7 ppm. The molecular ions identified in positive ESI-MS at m/z 236 $[M+H]^+$ allowed the deduction of its molecular weight of 235 g $mol^{-1}$.

Example 4 a) Synthesis of N-(2,4-dibromophenyl)-1H-benzimidazol-2-amine

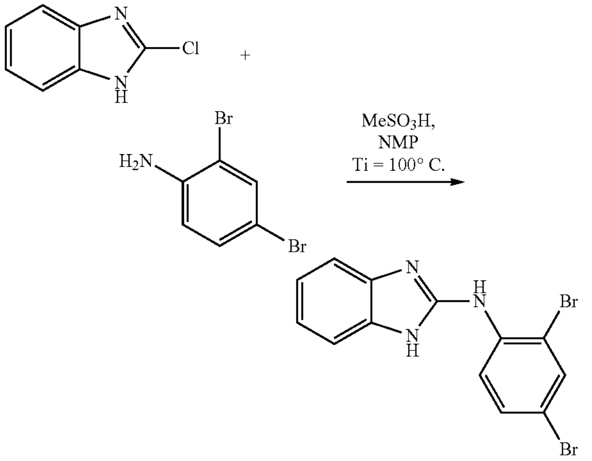

2-Chlorobenzimidazole (13.9 g, 90.8 mmol) and 2,4-dibromoaniline (25.1 g, 99.9 mmol) ire dissolved in NMP (45 mL) at 20° C. Methanesulfonic acid (9.6 g, 99.9 mmol) is added dropwise over ca. 0.5 h. The resulting suspension is heated to 100° C. and stirred until complete conversion of 2-chlorobenzimidazole. The reaction mixture is then cooled to 20° C., diluted with water (28 mL) and neutralized with 30 w-% aqueous sodium hydroxide (25.4 g, 190.5 mmol). The precipitated reaction product is isolated by filtration, washed with water and dried under vacuum at 90° C. Crude N-(2,4-dibromophenyl)-1H-benzimidazol-2-amine (33.6 g, 100%) is obtained as an off-white amorphous solid, which is further purified by recrystallization from methanol.

1H-NMR (DMSO-d6): δ=6.99-7.11 (m, 2H), 7.34-7.44 (m, 2H), 7.61 (dd, J=2.3, 8.9 Hz, 1H), 7.84 (d, J=2.3 Hz, 1H), 8.69 (d, J=8.9 Hz, 1H), 8.69 (brs, 1H), 11.16 (brs, 1H) ppm.

b) Synthesis of 2-bromo-5H-benzimidazolo[1,2-a] benzimidazole (I-3)

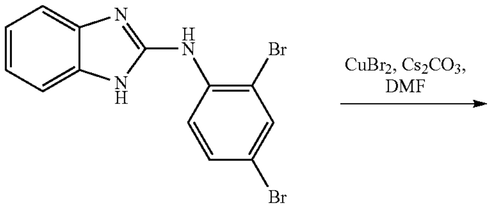

-continued

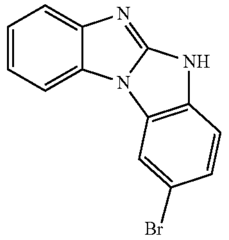

A suspension of cesium carbonate (13.3 g, 40.9 mmol) and copper(II) bromide (121.7 mg, 0.54 mmol) in DMF (48 mL) is heated to 130° C. A solution of N-(2,4-dibromophenyl)-1H-benzimidazol-2-amine (10.0 g, 27.2 mmol) in DMF (20 mL) is added dropwise over ca. 2 h. After complete conversion of N-(2,4-dibromophenyl)-1H-benzimidazol-2-amine, the reaction mixture is cooled to 20° C. and diluted with water. The precipitated reaction product is isolated by filtration, washed thoroughly with water and dried under vacuum at 100° C. Crude 2-bromo-5H-benzimidazolo[1,2-a]benzimidazole (7.9 g, 100%) is obtained as an off-white amorphous solid, which was further purified by recrystallization from DMF.

1H-NMR (DMSO-d6): δ=7.26 (t, J=7.6 Hz, 1H), 7.33 (t, J=7.6 Hz, 1H), 7.38-7.60 (m, 3H), 8.22 (d, J=7.7 Hz, 1H), 8.41 (brs, 1H), 12.18 (brs, 1H) ppm. 13C-NMR (DMSO-d6): δ=111.6, 111.8, 113.7, 114.0, 117.8, 120.0, 120.9, 123.9, 125.8, 128.2, 138.7 (brs), 143.6 (brs), 154.1 ppm. The molecular ions identified in positive ESI-MS at m/z 286 $[M+H]^+$ and m/z 288 $[M+H]^+$ allowed the deduction of its molecular weight of 286 g $mol^{-1}$.

Example 5 a) Synthesis of 5-bromo-N-(2,4-dibromophenyl)-1H-benzimidazol-2-amine

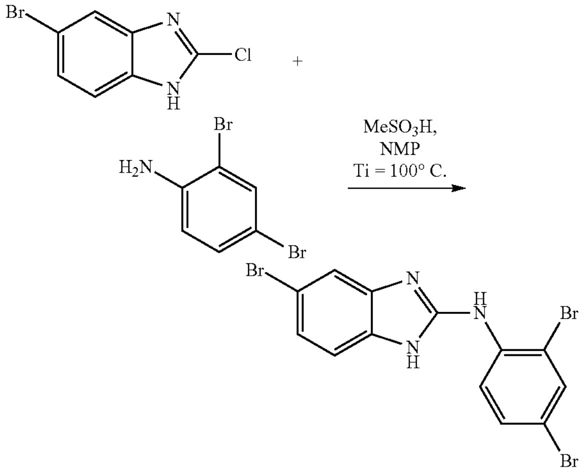

5-Bromo-2-chloro-1H-benzimidazole (10.0 g, 43.2 mmol) and 2,4-dibromoaniline (11.9 g, 47.5 mmol) are dissolved in NMP (22 mL) at 20° C. Methanesulfonic acid (4.6 g, 47.5 mmol) is added dropwise over ca. 0.5 h. The resulting suspension is heated to 100° C. and stirred until complete conversion of 5-Bromo-2-chloro-1H-benzimidazole. The reaction mixture is then cooled to 20° C., diluted with water (13 mL) and neutralized with 30 w-% aqueous sodium hydroxide (12.1 g, 90.8 mmol). The mixture is diluted with ethyl acetate (150 mL) and the aqueous phase separated. The organic phase is extracted with water (3×50 mL), dried over anhydrous sodium sulphate and evaporated to dryness. Crude 5-bromo-N-(2,4-dibromophenyl)-1H-benzimidazol-2-amine (23.5 g) is obtained as an off-white amorphous solid, which is further purified by recrystallization from methanol.

1H-NMR (DMSO-d6): δ=7.17 (dd, J=1.9, 8.4 Hz, 1H), 7.34 (d, J=8.4 Hz, 1H), 7.58 (brs, 1H), 7.61 (dd, J=2.3, 8.9 Hz, 1H), 7.86 (d, J=2.3 Hz, 1H), 8.60 (d, J=8.5 Hz, 1H), 8.76 (brs, 1H), 11.31 (brs, 1H) ppm.

b) Synthesis of 2,9- and 3,9-dibromo-6H-benzimidazolo[1,2-a]benzimidazole (I-6) & (I-7)

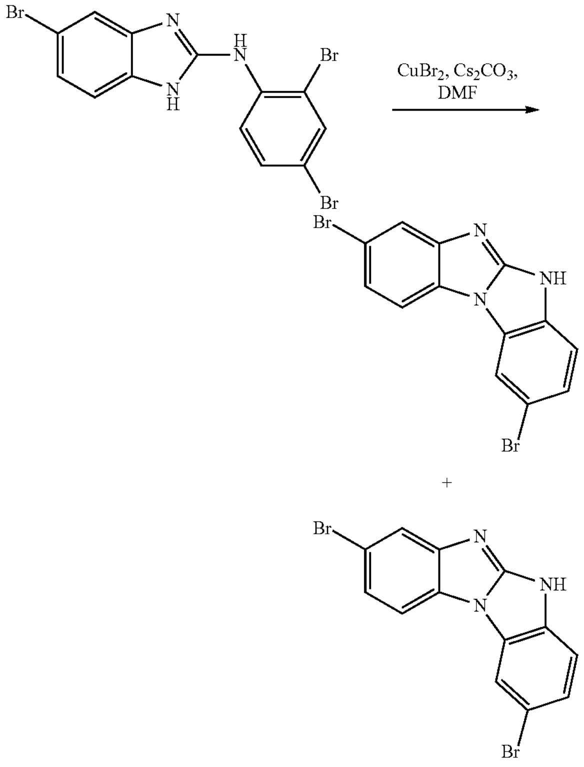

A suspension of cesium carbonate (11.2 g, 34.5 mmol) and copper(II) bromide (102.7 mg, 0.46 mmol) in DMF (39 mL) is heated to 130° C. A solution of 5-bromo-N-(2,4-dibromophenyl)-1H-benzimidazol-2-amine (10.3 g, 23.0 mmol) in DMF (18 mL) is added dropwise over ca. 1 h. After complete conversion of 5-bromo-N-(2,4-dibromophenyl)-1H-benzimidazol-2-amine, the reaction mixture is cooled to 20° C. and diluted with water. The precipitated reaction product is isolated by filtration, washed thoroughly with water and dried under vacuum at 100° C. Crude reaction product (4.5 g, 53%) is obtained as an off-white amorphous solid (mixture of isomers), which is further purified by recrystallization from acetic acid.

The molecular ions identified in positive ESI-MS at m/z 364 $[M]+H^+$, m/z 366 $[M+H]^+$ and m/z 368 $[M+H]^+$ allowed the deduction of its molecular weight of 365 g $mol^{-1}$.

The invention claimed is:

1. A process for the preparation of a compound of formula (I)

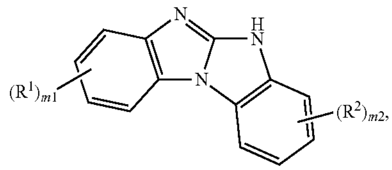

comprising a) heating a compound of formula

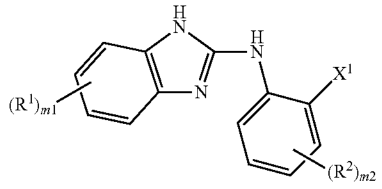

(II) in the presence of a catalyst and a base in a solvent at elevated temperature, wherein m1 is 0, or an integer 1 to 4, m2 is 0, or an integer 1 to 4, $X^1$ is Cl, Br, or I, $R^1$ and $R^2$ are independently of each other hydrogen, a halogen atom, a $C_1$-$C_{25}$alkyl group, which can optionally be substituted by E and or interrupted by D; a $C_1$-$C_{25}$alkoxy group, a group of formula $-(A^5)_v-(A^6)_s-(A^7)_t-(A^8)_u-R^{15}$, $—NR^{10}R^{11}$, or $Si(R^{12})(R^{13})(R^{14})$, v is 0, or 1, s is 0, or 1, t is 0, or 1, u is 0, or 1, $A^5$, $A^6$, $A^7$ and $A^8$ are independently of each other a $C_6$-$C_{24}$arylen group, which can optionally be substituted by G, or a $C_2$-$C_{30}$heteroarylen group, which can optionally be substituted by G; wherein $R^{10}$ and $R^{11}$ are independently of each other a $C_6$-$C_{24}$aryl group, which can optionally be substituted by G; or a $C_2$-$C_{30}$heteroaryl group, which can optionally be substituted by G;

$R^{12}$, $R^{13}$ and $R^{14}$ are independently of each other a $C_1$-$C_{25}$alkyl group, which can optionally be substituted by E and or interrupted by D; $C_6$-$C_{24}$aryl group, which can optionally be substituted by G; or a $C_2$-$C_{30}$heteroaryl group, which can optionally be substituted by G;

$R^{15}$ is a $C_6$-$C_{24}$aryl group, which can optionally be substituted by G; or a $C_2$-$C_{30}$heteroaryl group, which can optionally be substituted by G;

D is —S—, —SO—, $—SO_2—$, —O—, $—NR^{65}—$, $—SiR^{70}R^{71}—$, $—POR^{72}—$, $—CR^{63}{=}CR^{64}—$, or —C≡C—,

E is $—OR^{69}$, $—SR^{69}$, $—NR^{65}R^{66}$, $—CONR^{65}R^{66}$, or halogen,

G is E, or a $C_1$-$C_{18}$alkyl group, a $C_6$-$C_{24}$aryl group, a $C_6$-$C_{24}$aryl group, which is substituted by F, $C_1$-$C_{18}$alkyl, or $C_1$-$C_{18}$alkyl which is interrupted by O; a $C_2$-$C_{30}$heteroaryl group, or a $C_2$-$C_{30}$heteroaryl group, which is substituted by F, $C_1$-$C_{18}$alkyl, or $C_1$-$C_{18}$alkyl which is interrupted by O;

$R^{63}$ and $R^{64}$ are independently of each other H, $C_6$-$C_{18}$aryl; $C_6$-$C_{18}$aryl which is substituted by $C_1$-$C_{18}$alkyl, $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl.

2. The process according to claim 1, wherein the catalyst is selected from CuI, and $CuBr_2$ and the catalyst comprises optionally a ligand.

3. The process according to claim 1, wherein the base is selected from $Cs_2CO_3$, and $K_2CO_3$.

4. The process according to claim 1, wherein the solvent is selected from dimethoxymethane, diethoxyethane, 1,3-dioxane, 1,4-dioxane, N-methylpyrrolidinone, N,N-dimethylacetamide, dimethylformamide, and mixtures of these solvents.

5. The process according to claim 1, comprising reacting a compound of formula (III)

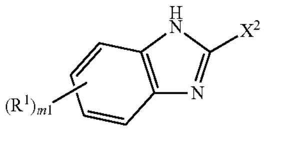

with a compound of formula (IV)

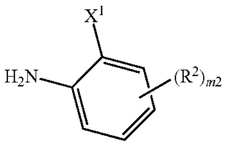

in the presence of an acid in a solvent at elevated temperature to obtain a compound of formula (II), wherein $X^2$ is Cl, Br, or I, and m1, m2, $R^1$, $R^2$ and $X^1$ are defined in claim 1.

6. The process according to claim 5, wherein the acid is selected from methane sulfonic acid, campher sulfonic acid, p-toluene sulfonic acid hydrochloric acid, and sulfuric acid.

7. The process according to claim 5, wherein the solvent is selected from dimethoxymethane, diethoxyethane, 1,3-dioxane, 1,4-dioxane, N-methyl-pyrrolidinone, N,N-dimethylacetamide, dimethylformamide, and mixtures of these solvents.

8. The process according to claim 1, wherein m1 and m2 are 0.

9. The process according to claim 1, wherein the compound of formula (I) is a compound of formula (Ia)

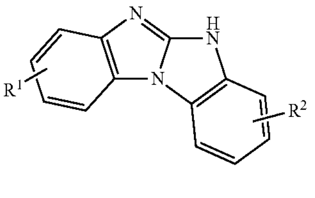

and the compound of formula (II) is a compound of formula (IIa)

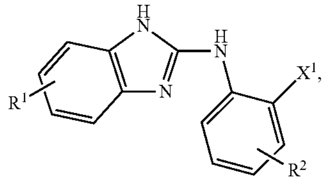

wherein $X^1$ is Cl, Br, or I, $R^1$ is hydrogen, $C_1$-$C_8$alkyl, $C_1$-$C_8$alkoxy, Br, Cl, or F, and $R^2$ is hydrogen, $C_1$-$C_8$alkyl, $C_1$-$C_8$alkoxy, Br, Cl, or F.

10. A process for the preparation of a compound of formula (VII)

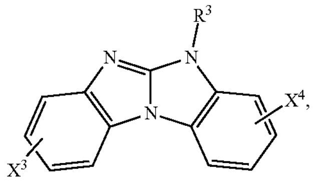

comprising halogenating a compound of formula (VI)

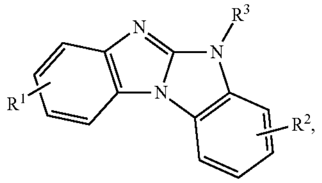

wherein $R^1$ and $R^2$ are H, $X^3$ is Br, or I and $X^4$ is H, Br, or I, $R^3$ is a group of formula $-(A^1)_o-(A^2)_p-(A^3)_q-(A^4)_r-R^{16}$, o is 0, or 1, p is 0, or 1, q is 0, or 1, r is 0, or 1, $R^{16}$ is a $C_6$-$C_{24}$aryl group, which can optionally be substituted by G; or a $C_2$-$C_{30}$heteroaryl group, which can optionally be substituted by G, $A^1$, $A^2$, $A^3$ and $A^4$ are independently of each other a $C_6$-$C_{24}$arylen group, which can optionally be substituted by G, or a $C_2$-$C_{30}$heteroarylen group, which can optionally be substituted by G, G is E, or a $C_1$-$C_{18}$alkyl group, a $C_6$-$C_{24}$aryl group, a $C_6$-$C_{24}$aryl group, which is substituted by F, $C_1$-$C_{18}$alkyl, or $C_1$-$C_{18}$alkyl which is interrupted by O; a $C_2$-$C_{30}$heteroaryl group, or a $C_2$-$C_{30}$heteroaryl group, which is substituted by F, $C_1$-$C_{18}$alkyl, or $C_1$-$C_{18}$alkyl which is interrupted by O, E is —$OR^{69}$, —$SR^{69}$, —$NR^{65}R^{66}$, —$CONR^{65}R^{66}$, or halogen, $R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, and $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—.

11. The process according to claim 10, comprising reacting a compound of formula
c1)
(Ia)
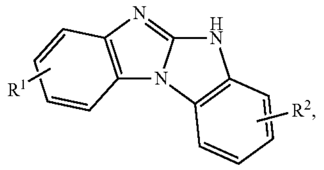
with a compound of formula $R^3$—$X^3$ (V), to obtain a compound of formula
(VI)
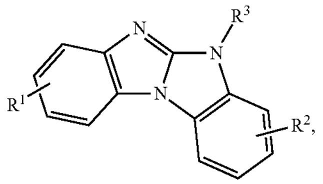
wherein $X^3$ is Cl, Br, or I, and
$R^1$, $R^2$, and $R^3$ are defined in claim 10.
* * * * *